United States Patent [19]
Renoux et al.

[11] Patent Number: 4,529,543
[45] Date of Patent: Jul. 16, 1985

[54] HEPATOSIN

[75] Inventors: Gerhard E. Renoux; Micheline J. Renoux, both of Tours, France

[73] Assignee: Newport Pharmaceuticals International, Calif.

[21] Appl. No.: 618,758

[22] Filed: Jun. 8, 1984

Related U.S. Application Data

[63] Continuation of Ser. No. 237,729, Feb. 24, 1981, abandoned.

[51] Int. Cl.³ .................... C07G 7/00; C07C 103/52; A61K 39/00; A61K 37/00
[52] U.S. Cl. .................... 260/112 R; 260/112.5 R; 424/85; 514/21
[58] Field of Search .................... 260/112.5 R, 112 R; 424/177, 85, 95; 514/21

[56] References Cited

U.S. PATENT DOCUMENTS

| | | | |
|---|---|---|---|
| 3,944,659 | 3/1976 | Folkers et al. | 424/95 |
| 3,975,237 | 8/1976 | Rubenstein et al. | 435/7 |
| 4,161,522 | 7/1979 | Hamburger | 260/112.5 R |
| 4,171,299 | 10/1979 | Hamburger | 260/112.5 R |
| 4,343,734 | 8/1982 | Lian et al. | 424/85 |
| 4,415,491 | 11/1983 | Vyas | 434/177 |
| 4,427,658 | 1/1984 | Maubois et al. | 424/177 |

Primary Examiner—Delbert R. Phillips
Attorney, Agent, or Firm—Cushman, Darby & Cushman

[57] ABSTRACT

A polypeptide-like material is prepared from liver cells and is named hepatosin. Hepatosin acts as an immune modulator or immunorestorative agent.

19 Claims, 3 Drawing Figures

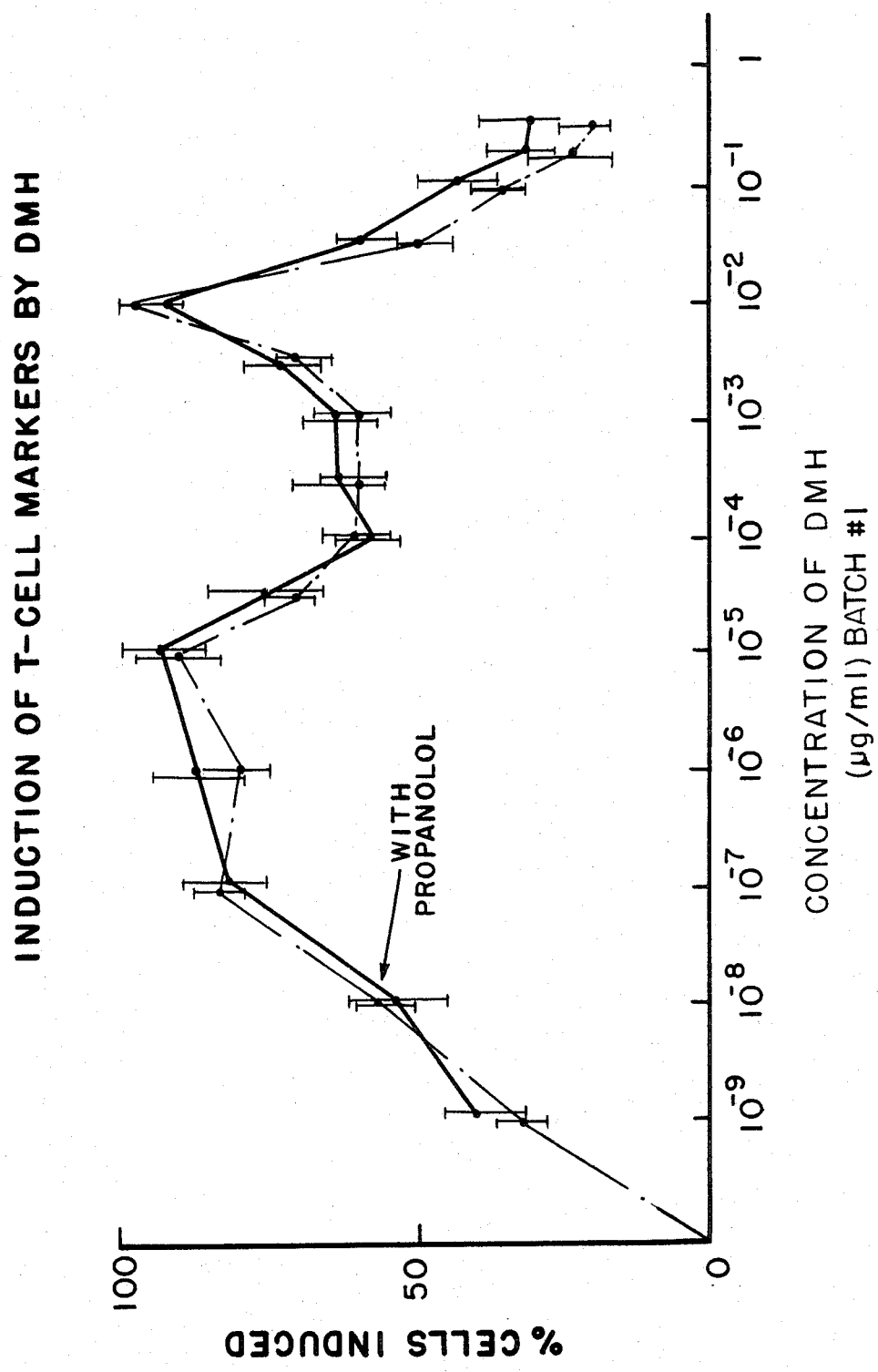

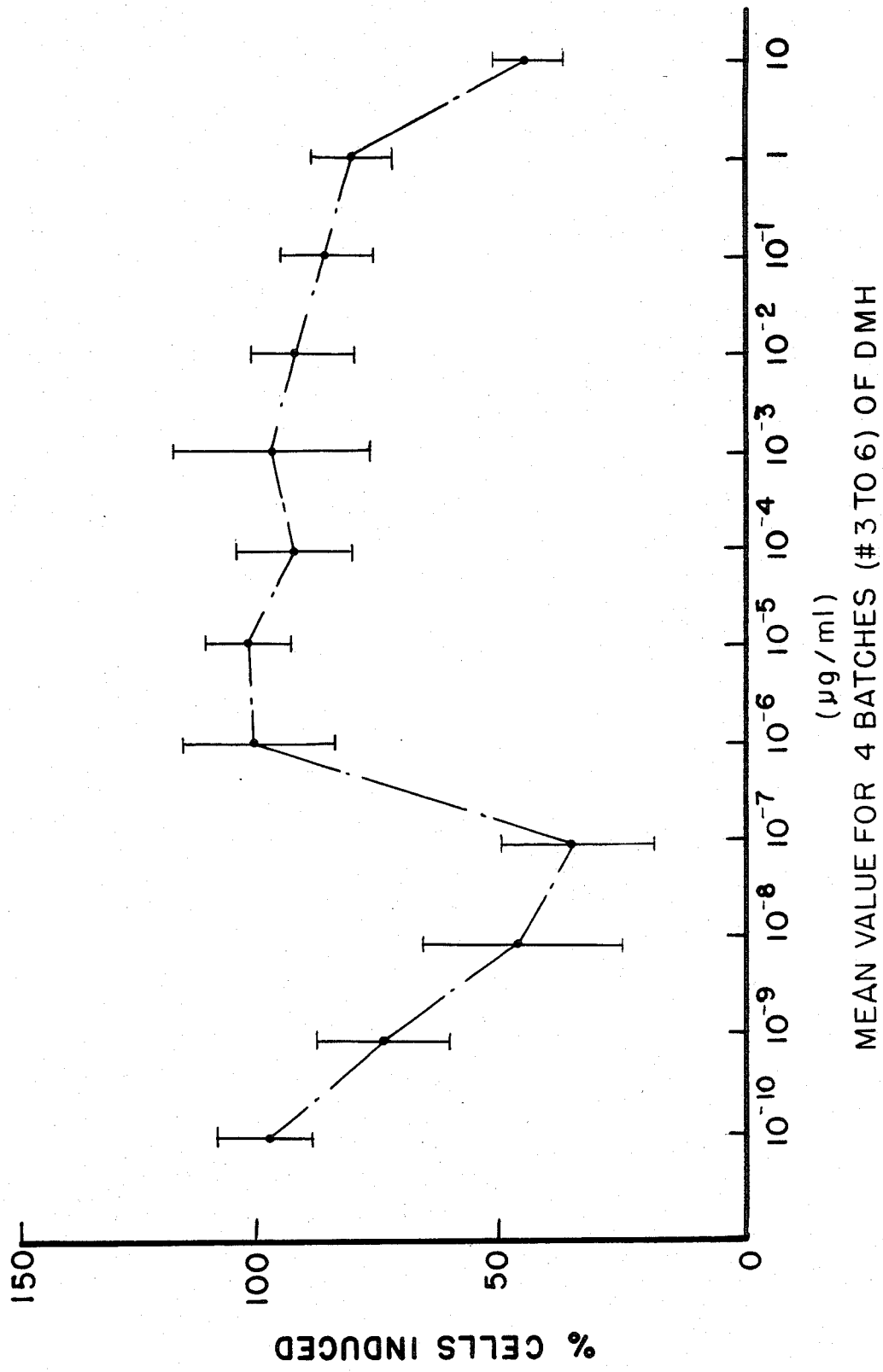

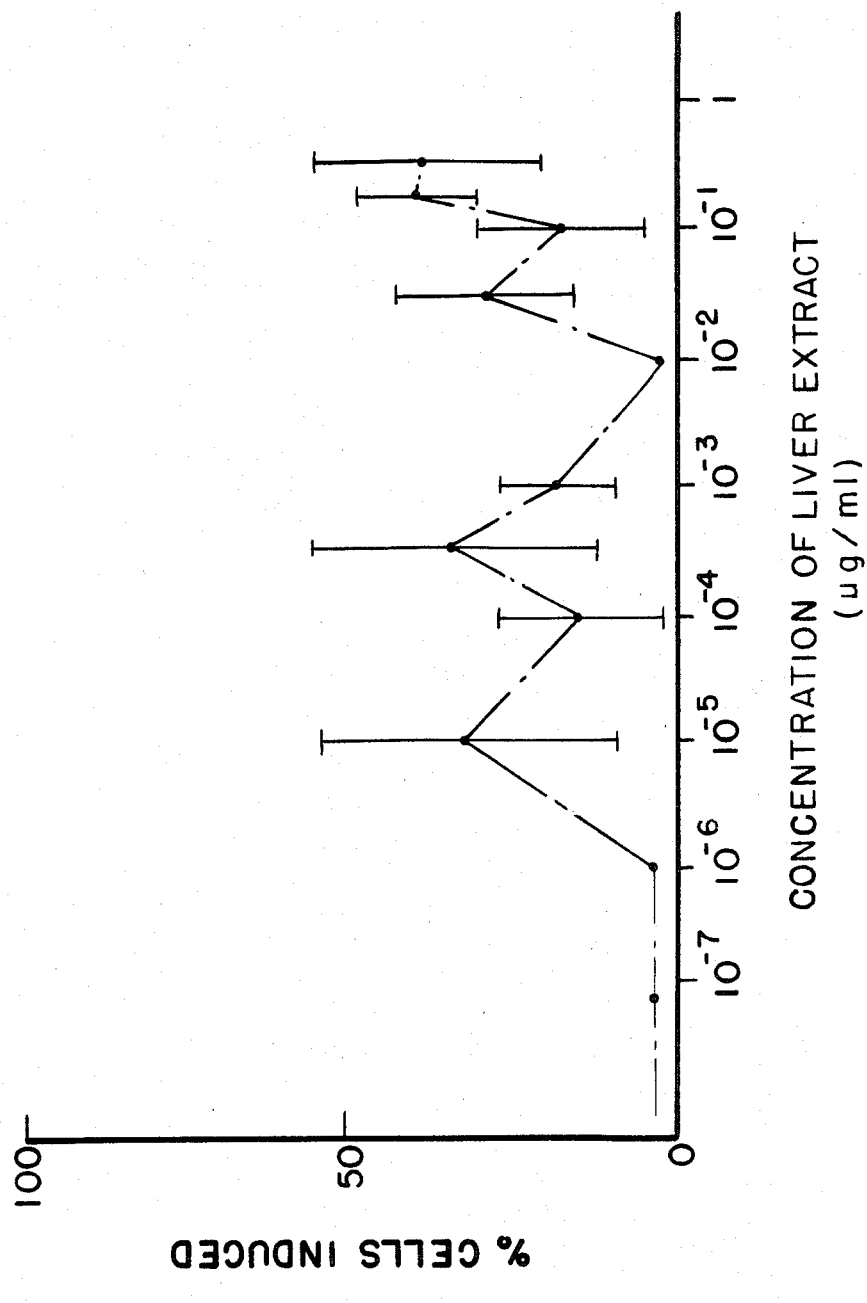

HEPATOSIN

This is a continuation of application Ser. No. 237,729, filed Feb. 24, 1981, now abandoned.

BACKGROUND OF THE INVENTION

Three general approaches have been used in recent times for drug development (1) screening large numbers of synthetic test compounds of diverse chemical structure (2) mimicking nature by designing compounds that exert an effect similar to a naturally occurring substance and (3) modifying the structure of an already known drug to maximize or improve one property or minimize an undesirable property. Classically, however, isolation of active principles from biological materials has been quite successful in producing therapeutically useful substances. The isolation of insulin from pancreas glands, quinine from Cinchona bark, and within the field of immunology, the isolation of polypeptide-like materials (Thymosin V, Thymopoietin) derived from the thymus gland which are able to restore or augment depressed immunity are a few examples. A method for restoration of depressed immunity can be medically useful in any disease in which a primary immunodeficiency exists or a secondary immunodeficiency is produced.

The discovery of hormones derived from the thymus and their use in medicine has recently become important and there is considerable literature thereon, for example:

Goldstein U.S. Pat. No. 4,002,740
Goldstein U.S. Pat. No. 4,079,127
DeSomer U.S. Pat. No. 3,438,859
Goldstein U.S. Pat. No. 4,082,737
Yeshiva British Pat. No. 1,195,980
Brunetti U.S. Pat. No. 3,657,417
Goldstein U.S. Pat. No. 4,002,602
Goldstein U.S. Pat. No. 4,077,949
Renoux, The Journal of Experimental Medicine, Vol. 145 (1977) pages 466-471

The entire disclosure of the above U.S. patents, British patent and Renoux article are hereby incorporated by reference and relied upon.

SUMMARY OF THE INVENTION

In the present invention, there is described for the first time the isolation of a novel polypeptide-like substance that is *not* derived from the thymus, that can be produced by liver cells in culture and can be found in the serum of all species that can be used to enhance immunity in aminals. The results presented herein demonstrate that (1) the novel biologically derived substance can be used to enhance cellular immunity (2) the origin of this substance is extra thymic (liver) and (3) assay of the material in serum can be used as a measure of immune competence. The new material is called hepatosin.

BRIEF DESCRIPTION OF THE DRAWING

FIG. 1 is a graph of the induction of T-cell Markers by hepatosin (identified as DMH) prepared in the presence of diethyldithiocarbamate (DTC);

FIG. 2 is a similar graph for the mean values for four batches of hepatosin (DMH); and FIG. 3 is a graph of the induction of T-Cell Markers similar to FIG. 1 but with hepatosin prepared in the absence of DTC.

DETAILED DESCRIPTION

Example 1

Preliminary assays revealed that when $C_3H$ mouse liver cells were cultured for 24 hours in the presence of the sodium salt of diethyldithiocarbamate (DTC), a soluble factor (hormone) was produced which was able to increase the immune responsiveness of $C_3H/He$ female mice to immunization with sheep red cells (SRC). The preparation of this "differentiating and maturing hormone" (DMH) which is given the name hepatosin was carried out by a technique summarized as follows: Livers were aseptically removed by passage through a sterile steel mesh. Fifty million liver cells were suspended in 50 ml of RPMI-1640 supplemented with 1% L-glutamine (But without fetal calf serum, antibiotics or phenol red) and $10^{-5}$ mM/ml (millimoles per ml) of DTC, and cultured in tissue culture flasks (#3075 Costar, Cambridge, Mass.). After 24 hours of incubation at 37° C. in an atmosphere of 95% air, 5% $CO_2$ and saturated vapor, supernatants were harvested by centrifugation at 4° C. Aliquots were tested for trypan blue tests (more than 95% viable liver cells at the time of harvest), cultured on trypticase-soy agar and tested for Limulus assays to discard any batch evidencing bacterial contamination or measurable endotoxin-like activity. Supernatants were heated at 100° C. for 1 hour, kept overnight at 4° C. and spun in the cold in a refrigerated PR-J International Centrifuge. The clear supernatant was purified by concentration on an UM05 membrane to discard salts, free amino acids and residual DTC. The active fraction, DMH, passed through a UM 05 membrane, thus indicating a molecular weight less than 5000. The concentrate contained 40 to 45 mg (dry weight) per ml and was filtered through a 0.43μ membrane before use. The biological activity of this preparation of DMH is described below under "Biological Activity". Unless otherwise indicated the biological data was obtained on the product obtained using the $C_3H$ mouse liver cells.

Example 2

Production of DMH by liver cells of nu/nu mice (athymic)

Liver cells ($10^6$ cells) were cultured in media as in Example 1 in the presence of $10^{-5}$ mM of DTC per ml. The final product was obtained after centrifugation and filtration through UM5 membranes to discard salts, free amino acids, etc . . . and through a UM10 membrane (MW higher than 500, less than 10,000).

Example 3

The incubation was carried out in the absence of DTC. The procedure otherwise was as in Example 1. There was obtained a product having similar properties to DMH but in an amount equivalent to 1% of the level obtained using DTC.

Hepatosin has a molecular weight between 500 and 5000 as shown by ultrafiltration studies, is resistant to heating at 100° C. and has an amino acid composition of aspartic acid, threonine, glutamic acid, glycine, cystine, tyrosine, phenylalanine and lysine.

In place of DTC to enhance the amount of hepatosin formed there can be used other immunopotentiators agents such as levamisole (The Merck Index 9th edition compound No. 8949) or Inosiplex (The Merck Index 9th edition Compound No., 4853, available under the trademark Isoprinosine and described in Gordon U.S. Pat. No. 3,646,007.

The range in amount of DTC (or other immunomodulator)employed with the medium for example can be from $10^{-3}$ to $10^{-12}$ mM/ml.

The incubation time is preferably 24 hours but can be varied, e.g. from 18 to 72 hours.

While incubation is preferably carried out at about 37° C. it can be carried out at other temperatures, e.g., 20° C.

In Example 1 the aliquots were tested simply to make sure the cells were alive. The culturing was to make sure there was no bacterial contamination. The heating to 100° C. was to eliminate chemical contaminants. Thus heating precipitates and denatures the contaminants.

Biological Properties

Hepatosin (DMH) is a polypeptide material which is able to cause precursor cells destined to become T-cells to differentiate into t-cells and to mature to the extent of being able to possess the functional properties of a T-cell.

(A) Differentiation (1) In Vitro (a) Induction of thy-1+Marker on precursor spleen cells from nu/nu mice Using the assay of Kumuro-Boyse, $5 \times 10^6$ spleen cells isolated from nu/nu mice were incubated at 37° C. in a 5% $CO_2$ atmosphere for 3.5 hours. The appearance of Thy-1+(T-cell marker) was measured at varying concentrations of DMH and was expressed as % of maximum induction observed in each individual assay since the maximum induction varied between 20-26%. Induction of CR+(B-cell marker) was not seen upon incubation of nu/nu cells in DMH, and even after a 18 hr. incubation.

The data presented in FIG. 1 demonstrated that maximal induction occurred at $10^{-7}$ μg/ml with significant induction occurring at $10^{-9}$ μg/ml. This activity was greater than that observed for the thymic hormones on a μg/ml basis. Propranolol (The Merck Index, 9th edition Compound No. 7628) a B-adrenergic blocking agent did not prevent induction. The propranolol was used in an amount of $10^{-5}$ mM/ml. The continuous line curve was the one with propranolol.

The data shown in FIG. 2 gave a somewhat different dose response curve and shows the mean values obtained for four batches of DMH. Activity was still seen at $10^{-9}$ μg/ml and maximal effects were noted at $10^{-6}$ μg/ml. The double peak dose response curve might signify that the DMH preparation was impure or could be evidence of a dual receptor system on the cell surface.

The data presented in FIG. 3 were obtained from a liver culture supernatant (LCS) prepared in the same manner as DMH, but produced in the absence of DTC in the culture media. It is obvious that some induction capacity existed in these cell supernatants, but the capacity was much less than when DTC was added.

(b) Induction of T-cell from precusor human peripheral blood null cells (acquisition of HTLA antigen)

To further test the hormone-like response of DMH, there was studied its effectiveness in recruiting T-cells from Null cells of human peripheral blood.

Human peripheral blood cells were purified on Ficoll-Hypaque density gardient and deprived of T-cells by two subsequent E rosetting and Ficol-Hypaque gradients. After two washes with RPMI medium, the sedimented pellet was adjusted to a final cell concentration of $2 \times 10^6$/ml in a total volume of 0.25 ml RPMI-Hepes+FCS with complement removed.

DMH, "normal liver supernatant", and Thymosine V were added at the levels indicated on Table 1. Microcytoxicity tests were performed using anti-HTLA serum and rabbit complement, after five hours incubation in a moisturized 5% $CO_2$ atmosphere.

As shown in Table 1, as low as 10 μl/ml of DMH induced acquisition of a T-cell surface marker in the null cell stock of human peripheral blood cells. The supernatant from non-conditioned liver cells was inactive.

TABLE 1

| In Vitro Generation of HTLA+ Cells Human Peripheral Blood Cells | | | |
|---|---|---|---|
| Treatment | | % net increase[a] | |
| | (μl/ml) | Exp. 1 | Exp. 2 |
| DMH | 10 | 27.0 | 27.4 |
| | 50 | 20.5 | 18.0 |
| Liver | 10 | 2.0 | 1.0 |
| | 50 | 0 | 0 |
| Thymosin V | 50 | 5 | NT (not tested) |

[a]Controls: 5 to 8%

(c) Differentiation induced in bone-marrow cells

T-cells and B-cells are derived from bone-marrow stem cells. It was found that DMH induces Thy-1+ cells from bone marrow precusor cells in a variety of mouse strains, including nu/nu mice, to a greater extent than thymosin V. as summarized in Table 2.

Induction assays were performed as above : 2.5 hours of incubation for Thy-1 cytotoxicity assays and 6 hours of incubation at 37° C. in a 5% $CO_2$ atmosphere for CR+ B-cells, with the doses of DMH indicated in Table 2 for $5 \times 10^6$ bone-marrow cells.

TABLE 2

| | Effect of DMH on Induction of Thy-1+ on Bone Marrow Precursor Cells. | | | | | | | | | |
|---|---|---|---|---|---|---|---|---|---|---|
| | Treatment | 6-8 w. old nu/nu | | 6-8 w. old C3H/He | | 6-8 w. old Balb/C | | 11-12 w. old Balb/C | | 6-8 w. old C57BL/6(2) | |
| | (ml/ml) | Thy-1+ | CR+ | Thy-1+ | CR+ | Thy-1+ | CR+ | Thy-1+ | CR+ | Thy-1+ | CR+ |
| DMH | 0.25 | 0 | 0 | 0 | 0 | 2 | 0 | 0 | 0 | 0 | 2 |
| | 2.5 | 3.3 | 0 | 2.6 | 0.7 | 8 | 0 | 4 | 0 | 6 | 2 |
| | 25 | 7.5 | 0 | 6.5 | 0 | 3 | 1 | 15 | 0 | 4 | 2 |
| | 250 | — | — | 0 | 0 | 1 | 0 | 2 | 0 | 0 | 0 |
| Thymosine | 125 | 1.5 | 2.8 | 3.5 | 1.2 | 0 | 3 | 12 | 3 | 1 | 3 |

In summary, the data in Table 2 demonstrates that on nu/nu spleen lymphocytes, DMH recruits T-cells from the precursor stock in bone-marrow, without modifying the B-cell lineage; however, the dose-effect curve of DMH might depend upon the strain and age of animal.

(2) In Vivo induction of T-cell differential in nu/nu mice

Assays were performed by ip (intraperitoneal) administration of 0.25 ml of DMH to nu/nu mice (6 to 8 weeks of age). Counts for Thy-1+ cells or for B cells (Ig+, CR+) were performed on the fourth day. Controls included untreated mice and animals treated with the supernatant of liver cells cultured without sodium diethyldithiocarbamate (DTC).

As shown in Table 3, DMH induced a high percentage of mature T-cells (Thy-1+), in nu/nu mice, which compared favorably with the effects of known thymus hormones, inactive in vivo, without modifying the number of B cells, in contrast with other "hormones" (thymopoietin, thymic serum factor, TFS).

TABLE 3

In Vivo Effects of DMH on Induction of Thy-1 In Splenocytes of nu/nu Mice

| Treatment | % specific marker | |
|---|---|---|
| | Thy-1+ | Ig+ |
| none | 2-5 | 24-32 |
| Liver alone | 2-6 | 26-34 |
| DMH | 15-27 | 27-34 |

G. Goldstein et al. (Science 1979, 204, 1309) described a synthetic pentapeptide, TP5, derived from thymopoietin, stated as possessing the same activities as thymopoietin.

J. F. Bach et al. (Nature, 1977, 266, 55) described FTS a nonapeptide, stated as being the thymic hormone.

None of these prior products possesses in vivo activities to induce the Thy-1+ phenotype in precursor cells present in the spleen of nu/nu mice as we show above in Table 3.

Nu/nu mice (C57BL/6 background) were treated with 0.1 to 10 μg/mouse DMH and the activity compared with Thymopoietin and FTS. Mice were sacrificed four days later, and Thy-1.2+ and CR+ cells were enumerated in the spleen (four mice per group).

TABLE 4

| Treatment (μg/mouse) | % of Cells Induced | |
|---|---|---|
| | Thy-1+* | CR+ |
| Saline | 0 | 33-38 |
| DMH 10 | 16-26 | 38-40 |
| 1 | 19-19 | 34-38 |
| 0.1 | 3-12 | 31-36 |
| FTS 10 | 0 | 38-39 |
| 1 | 0 | 28-39 |
| 0.1 | 0 | 26-34 |
| TP5 10 | 0 | 40-43 |
| 1 | 0 | 12-26 |
| 0.1 | 0 | 13-37 |

Background = Thy-1+ cells: 2-6 (four mice per group)* = net increase.

None of the doses modified the background number of CR+ cells (controls: 27 to 35%), after a six hour incubation time.

A supernatant from liver cells cultured without DTC was completely unable to modify background numbers of T- or B-cells.

DMH is specifically active in recruiting T-cells from precommitted precursor cells in nu/nu mice, without effects on the B cell lineage, DMH was devoid of endotoxin-like products (negative Limulus tests).

(B) T-Cell functions increased or created by DMH (1) DMH - induced T-cell functions in nu/nu mice Thymusless, nu/nu mice, are unable to evoke IgG-antibody-forming spleen cells (PFC) in response to immunization with SRBC.

Nu/nu mouse lymphocytes did not proliferate in the presence of T-cell mitogens, such as PHA or Con A.

The effects of DMH upon the T-cell induced IgG-PFC production were studied in vivo by intraperitoneally administering 0.25% ml DMH at the time of iv (intravenous) immunization with $10^8$ SRBC with counts for splenic PFC made four days later (Table 5).

TABLE 5

Effect on DMH (In Vivo) on Differentiation and Functional T-cell Activities in nu/nu Mice

| Test | Treatment | |
|---|---|---|
| | None (Controls) | 0.25 ml DMH |
| Thy-1$^{30}$ (4) | <5 | 18 ± 3 |
| IgG-PFC (4) | 0 | 95 ± 7 |

The effect of DMH to modify mitogen-induced lymphoproliferation was studied in vitro by adding 0.01 ml DMH per ml culture medium ($5 \times 10^6$ live spleen cells) in the presence of, respectively 0.5 μg PHA, 0.5 μg Con A or 1:100 diluted PWM.

Table 6 summarizes the results of a typical series of assays evidencing increased functional T-cell-mediated responses in thymusless mice treated with DMH, whereas the PWM-induced lymphoproliferation, a B-cell response in mice, was impaired.

TABLE 6

| | IgG-PFC per spleen | In Vitro Responsiveness to | | |
|---|---|---|---|---|
| | | PHA | Con A | PWM |
| DMH-treated | 95 | 1029 ± 92 | 2604 ± 52 | 1851 ± 63 |
| Controls | 0 | 641 ± 23 | 1668 ± 38 | 2003 ± 68 |

(2) DMH elicits increased immune responses in nonresponder mice

Immunopotentiators, Levamisole and Isoprinosine (and to a lesser degree sodium diethyldithiocarbamate) are under a genetic control for responsiveness. For example, C3H/He mice are stimulated for increased responses to SRBC, while C57BL/6 mice remain insensitive to the effect of the agents.

Table 7 shows that 0.25 ml DMH i.p. administered at the time of immunization with $10^8$ SRBC significantly stimulated PFC production in both mouse strains.

TABLE 7

Effect of DMH on SRBC Antibody Production

| | C3H/He | | C57BL/6 | |
|---|---|---|---|---|
| | IgM | IgH | IgM | IgG |
| Treatment | 450 ± 70 | 51 ± 6 | 136 ± 58 | 17 ± 9 |
| DMH | 1035 ± 280 | 148 ± 50 | 1366 ± 270 | 53 ± 7 |

Therefore, a treatment with DMH could be indicated in patients unresponsive to immunotherapy.

(3) DMH increases Con A-induced lymphoproliferation

The effects on DMH of human peripheral blood cells (PBL) were compared with the effects of Thymosin, fraction V. In the first assay (Table 8), it was demonstrated that DMH increases the lymphoproliferation induced by a suboptimal dose of Con A at a level similar to FSV (thymosin fraction V).

TABLE 8
Effect of (In Vivo) DMH on Con A-induced Lymphoproliferation of PBL

| Controls | dpm 82824 | bgd 1212 | % increase above controls |
|---|---|---|---|
| +20 μg FSV | 104624 | 1890 | 126 |
| +10 μg DMH | 109018 | 1470 | 132 |

Three days of culture in the presence of 20 μg of Con A, PBL, human peripheral blood lymphocytes.

(4) Suppressor activities induced by DMH

The maturing efficacy of DMH on human lymphocytes was tested by evidencing the suppressor activities of DMH-treated cells on a two-way mixed lymphocyte culture (MLC) of two HLA unrelated healthy donors. The data were compared with the data obtained with FSV-treated cells from the same donor (donor A).

TABLE 9
Effect on DMH (2 μg) on Production of Suppressor Activity (Two-way MLC) in Human Lymphocytes

| Blasts added (× 10³) | cpm | % Suppression |
|---|---|---|
| 0 | 51,061 | 0 |
| 10 | 34,314 | 33 |
| 25 | 34,473 | 33 |
| 50 | 20,131 | 61 |
| 100 | 9,458 | 80 |

As shown in Table 9, DMH can induce suppressor activities against the allogenic antigen-induced lymphoproliferation at levels singificantly higher than those attained by FSV-treated blast cells.

The hepatosin (DMH) of this invention has been shown to induce mature functioning T-cells from precursor cells of the immune system, thus it is an immune modulator, or immunorestorative agent.

An immunopotentiator or immunomodulator is any agent which either restores depressed immune function, or enhances normal immune function, or both. Immune function is defined as the development and expression of humoral (antibody-mediated) immunity, cellular (thymocyte-mediated) immunity, or macrophage and granulocyte mediated resistance. It logically includes agents acting directly on cellular or molecular mechanisms which, in turn, act to modify the function of cells involved in immune response. Augumentation of immune function may result from the action of an agent to abrogate suppressive mechanisms derived by negative-feedback influences endogenous or exogenous to the immune system. Thus, immune potentiators have diverse mechanisms of action. Despite the diversity of cell site of action and biochemical mechanism of action of immunopotentiators, their applications are essentially the same; that is, to enhance host resistance.

Applications of Immunopotentiators

1. The principal protective function of the immune system relates to resistance to invasion by pathogens, including viruses, rickettsia, mycoplasma, bacterial fungi and parasites of all types. Thus, improvement of immune response, particularly when depressed, would calculatedly improve resistance in infection or infestation by any of the above pathogens. Animmune potentiator alone or in combination with anti-infective therapy can be applied to any or all infectious diseases.

2. A second protective function of the immune system is thought to be resistance to engraftment of foreign tissue, either natural as in fetal-maternal relationship; or unnatural as performed by the transplant physician. The use of immunopotentiators to facilitate rejection of fetal or placental tissues or to modify or induce tolerance to grafts is logical.

3. A third protective function of the immune system is thought to be resistance to malignant cell development as in cancer. The use of immunopotentiators in cancer is logical to enhance tumor rejection and to inhibit tumor recurrences following other forms of therapy.

4. A fourth protective function involves the capacity to recognize foreignness and to maintain non-reactivity to self by positive suppressor mechanisms. In auto-immune and related disorders, immune reactivity directed at self antigens or exaggerated, elevated responses are apparent which are self destructive. Immunopotentiators would logically be used to restore normal suppressor mechanisms, induce tolerance or otherwise promote a normal immune response.

Each of the protective functions of the immune system can be modified by nonspecific therapy with immunopotentiators alone or in combination with other agents employed to improve resistance or to kill the invading pathogen. In addition, specific resistance can be augmented by use of immunopotentiators in conjection with some form of antigen as in a vaccine employing, for example, virus, tumor cell, etc. This use can be to induce either specific immunity or tolerance. The latter might be exemplified by use with antigen in allergy or auto-immune disease. Use of immunopotentiators may be either therapeutic or prophylactic; the latter particularly in aging, where infection, auto-immunity, and cancer are more common. The timing of administration and routes are variable and may be critical in determining whether a positive or negative response results. Any agent capable of augmenting immune response may inhibit it depending on timing and dose; thus, under certain circumstances an immunopotentiator could be used as an immunosuppressive agent for use in allergy, autoimmunity and transplantation.

Thus the immunopotentiators of the invention can be employed, for example, to provide resistance to invasion by the viruses in the following Table.

TABLE

| Virus | Class | Disease |
|---|---|---|
| Arenavirus | RNA | Rift Valley Fever |
| Influenza | RNA | Influenza |
| Rhinovirus | RNA | Common Cold |
| Poliovirus | RNA | Polio |
| Measles | RNA | Rubella |
| Newcastles Disease Virus | RNA | Newcastles disease |
| Rotavirus | RNA | Gastroenteritis in infants |
| Hepatitis Type A | RNA | Infectious Hepatitis |
| Rabies virus | RNA | Rabies |
| Arbovirus | RNA | Encephalitis |
| Vaccinia virus | DNA | Smallpox |
| Herpes Simplex Virus | DNA | Cold sore, Encephalitis, Veneral Disease |
| Herpes Zoster | DNA | Shingles |
| Varicella Zoster | DNA | Chicken pox |
| Adenovirus | DNA | Respiratory |
| Hepatitis Type B | DNA | Chronic Hepatitis, Severe Hepatitis |
| Foot and Mouth Disease Virus | DNA | Foot and Mouth Disease |
| Machupo Virus | | Hemorrhagic Fever |

The compounds can also be used to treat conditions resulting from relative or absolute T-cell deficiencies such as DiGeorge Syndrome, fungal infections, mycoplasma infections, tuberculosis, leprosy, acute and chronic viral infections and systemic lupus erythemotosus.

Specifically hepatosin can be used to treat primary or secondary immunodeficiency. An example of primary immunodeficiency is genetic immunodeficiencies such as severe Combined Immunodeficiency (DIC). Examples of secondary immunodeficiency are deficiencies in the immune system caused by infections (viral, bacterial, parasitic, etc.), chemotherapy (treatment of cancer), radiation therapy (cancer), surgery (any major surgery), or nutritional or environmental factors.

The composition of the invention are useful in treating mammals (and cells of mammals) including humans, swine, dogs, cats, cattle, horses, sheep, goats, mice, rabbits, rats, guinea pigs, hamsters, monkeys, etc.

Unless otherwise indicated, all parts and percentages are by weight.

All temperatures are in degrees centigrade unless otherwise indicated.

The compositions can comprise, consist essentially of or consist of the materials set forth and the processes can comprise, consist essentially of or consist of the steps set forth with such materials.

The compositions can be administered to the mammals by conventional techniques, e.g. orally, nasally, rectally, vaginally, enterally or parenterally. They can be employed as injectable solutions, e.g., in water, or as tablets, pills, capsules, etc.

Being polypeptide in nature hepatosin can be administered by the parenteral route (im (intramuscularly), iv (intravenously), sc (subcutaneously)), and since hepatosin has a molecular weight of <5,000, it can be absorbed upon oral adminstration if protected from enzymatic degradation. The formulation for injection contains enough material to allow for administration to humans of 1–1000 μg/kg. Similar dosages can be used with the other animals.

Thus there is administered a therapeutically effective amount of the compound of the invention alone or in combination with a pharmaceutically acceptable carrier.

What is claimed is:

1. Hepatosin, a compound having a molecular weight between 500 and 5000, resistant to heating at 100° C. and having an amino acid composition of aspartic acid, threonine, glutamic acid, glycine, cystine, tyrosine, phenylalanine, and lysine, said hepatosin being capable of being obtained by culturing $C_3H$ mouse liver cells by suspending 50 million liver cells in 50 ml of RPMI-1640 supplemented with 1% L-glutamine and free from fetal calf serum, antibiotics, and phenol red at 37° C. for 24 hours in an atmosphere of 95% air, 5% $CO_2$, followed by harvesting by centrifugation.

2. A method of preparing the hepatosin of claim 1 comprising culturing $C_3H$ mouse liver cells by suspending 50 million liver cells ion the medium RPMI-1640 supplemented with L-glutamine and free from fetal calf serum, antibiotics and phenol red at 37° C. for 24 hours in an atmosphere of 95% air, 5% $CO_2$, followed by harvesting by centrifugation and recovering the hepatosin thus prepared.

3. A method according to claim 2 wherein the culture medium includes an immunopotentiator in an amount sufficient to enhance the yield of hepatosin.

4. A method according to claim 3 wherein the immunopotentiator is diethyldithiocarbamic acid or a salt thereof, levamisole of inosiflex.

5. A method according to claim 3 wherein the immunopotentiator is the sodium salt of diethyldithiocarbamic acid.

6. A composition containing the hepatosin of claim 1 in a concentration at least about 100 times as great as it is obtained by culturing $C_3H$ mouse liver cells by suspending 50 million liver cells in 50 ml of RPMI-1640 supplemented with 1% L-glutamine and free from fetal calf serum, antibiotics and phenol red at 37° C. for 24 hours in an atmosphere of 95% air, 5% $CO_2$, followed by harvesting by centrifugation.

7. A liquid composition containing the hepatosin of claim 1 in an amount of at least 40 mg/ml.

8. A composition according to claim 7 which is an aqueous liquid composition.

9. A method of imparting immunomodulating activity or, antiviral activity or comprising administering to a mammal an effective amount for such puroppose of the hepatosin of claim 1.

10. A method according to claim 9 of imparting immunomodulating activity comprising administering to a mammal an effective amount of such purpose of the hepatosin of claim 1.

11. A method according to claim 9 of imparting antiviral activity comprising administering to a mammal an effective amount of such purpose of the hepatosin of claim 1.

12. A liquid composition containing the hepatosin of claim 1 in an amount of at least 40 mg/ml.

13. A method of imparting immunomodulating activity or antiviral activity comprising administering to a mammal an effective amount for such purpose of the hepatosin of claim 1.

14. A method for reconstituting immune functions in a thymic deprived or immunodeprived mammal which method comprises administering to said mammal an immunopotentiating effective amount of the hepatosin claim 1.

15. A method for the treatment of a condition in a mammal resulting from relative or absolute T-cell deficiencies, which comprises administering a therapeutically effective amount of the hepatosin of claim 1.

16. A method for the treatment of a primary or secondary immunodeficiency in a mammal comprising administering to the mammal an effective amount for such purpose of the hepatosin of claim 1.

17. A method according to claim 15 of treating primary immunodeficiency.

18. A method according to claim 15 of treating secondary ummunodeficiency.

19. A method according to claim 9, wherein the dosage administered is 1–1000 μg/kg body weight of the mammal.

* * * * *

UNITED STATES PATENT AND TRADEMARK OFFICE
CERTIFICATE OF CORRECTION

PATENT NO. : 4,529,543
DATED : July 16, 1985
INVENTOR(S) : Gerard Renoux and Micheline Renoux It is certified that error appears in the above-identified patent and that said Letters Patent is hereby corrected as shown below:

IN THE NAME:

In the name of the first inventor change "Gerhard" to --Gerard--.

Signed and Sealed this

Twenty-second Day of April 1986

[SEAL]

Attest:

DONALD J. QUIGG

Attesting Officer

Commissioner of Patents and Trademarks